(12) United States Patent
Shishimi et al.

(10) Patent No.: US 12,145,903 B2
(45) Date of Patent: Nov. 19, 2024

(54) METHOD FOR PRODUCING 2,4-DIALKYLBENZALDEHYDE

(71) Applicant: MITSUBISHI GAS CHEMICAL COMPANY, INC., Chiyoda-ku (JP)

(72) Inventors: Toru Shishimi, Okayama (JP); Tatsuya Utamura, Okayama (JP); Yutaka Matsuura, Niigata (JP); Shinichi Nagao, Kanagawa (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 17/769,151

(22) PCT Filed: Oct. 16, 2020

(86) PCT No.: PCT/JP2020/039007
§ 371 (c)(1),
(2) Date: Apr. 14, 2022

(87) PCT Pub. No.: WO2021/075518
PCT Pub. Date: Apr. 22, 2021

(65) Prior Publication Data
US 2024/0132434 A1    Apr. 25, 2024

(30) Foreign Application Priority Data

Oct. 17, 2019    (JP) ................ 2019-190254

(51) Int. Cl.
*C07C 45/49*    (2006.01)

(52) U.S. Cl.
CPC ................ *C07C 45/49* (2013.01)

(58) Field of Classification Search
CPC .................................. C07C 45/49
See application file for complete search history.

(56) References Cited

U.S. PATENT DOCUMENTS

| | | | |
|---|---|---|---|
| 3,962,343 A | 6/1976 | Fujiyama et al. | |
| 4,460,794 A * | 7/1984 | Fujiyama | C07C 45/49 568/428 |
| 5,395,978 A | 3/1995 | Weisse et al. | |
| 7,154,008 B2 * | 12/2006 | Kato | C07C 45/49 568/433 |
| 2004/0092776 A1 | 5/2004 | Kato et al. | |
| 2005/0085670 A1 | 4/2005 | Kato et al. | |
| 2009/0118547 A1 | 5/2009 | Kitamura et al. | |
| 2018/0282662 A1 | 10/2018 | Chi-Lam et al. | |

FOREIGN PATENT DOCUMENTS

| | | |
|---|---|---|
| CN | 101437784 A | 5/2009 |
| JP | 50-5344 A | 1/1975 |
| JP | 6-234692 A | 8/1994 |
| JP | 2004-43362 A | 2/2004 |
| JP | 2005-120037 A | 5/2005 |
| JP | 2017-533926 A | 11/2017 |

OTHER PUBLICATIONS

International Search report issued Dec. 1, 2020 in PCT/JP2020/039007, filed on Oct. 16, 2020, 3 pages.
Crounse, "The Gattermann-Koch Reaction: The Formylation of Isopropylbenzene under Pressure", Journal of the American Chemical Society, vol. 71, No. 4, 1949, 2 pages.

* cited by examiner

*Primary Examiner* — Sikarl A Witherspoon
(74) *Attorney, Agent, or Firm* — Oblon, McClelland, Maier & Neustadt, L.L.P.

(57) ABSTRACT

An object of the present invention is to provide a method for producing 2,4-dialkylbenzaldehyde with excellent conversion rate and yield, and excellent regioselectivity for formylation, by allowing carbon monoxide to react on a starting material containing a specific m-dialkylbenzene in the presence of hydrogen fluoride and boron trifluoride. The method for producing 2,4-dialkylbenzaldehyde according to the present invention comprises a step of allowing carbon monoxide to react on a starting material containing m-dialkylbenzene represented by formula (1) in the presence of hydrogen fluoride and boron trifluoride for formylation at least at a position (a), wherein the starting material is a dialkylbenzene containing more than 90 mol % of m-dialkylbenzene represented by formula (1), and the number of moles of boron trifluoride relative to 1 mole of m-dialkylbenzene represented by formula (1) is 0.7 mol or more and 3.0 mol or less:

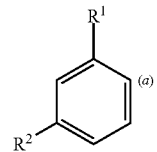

(1)

a wherein $R^1$ represents an alkyl group having 1 or more and 3 or less carbon atoms, and $R^2$ represents a chain or cyclic alkyl group having 2 or more and 7 or less carbon atoms, with a secondary or tertiary carbon at the benzylic position, provided that the number of carbons of $R^2$ is larger than the number of carbons of $R^1$.

21 Claims, No Drawings

METHOD FOR PRODUCING 2,4-DIALKYLBENZALDEHYDE

CROSS-REFERENCE TO RELATED APPLICATIONS

The present application is a 35 U.S.C. § 371 national stage application of International patent application PCT/JP2020/039007, filed Oct. 16, 2020, which is based on and claims the benefit of priority to Japanese Application No. 2019-190254, filed Oct. 17, 2019. The entire contents of these applications are incorporated herein by reference.

TECHNICAL FIELD

The present invention relates to a method for producing 2,4-dialkylbenzaldehyde.

BACKGROUND ART

Conventionally, alkylbenzaldehydes have been attracting attention for their use as fragrances and as starting materials for fragrances, and in these applications, not only aroma but also low skin sensitization and having biodegradability are of importance, and the substitution position of the substituent and the abundance ratio of the isomers are important for these properties.

PTL 1 describes allowing carbon monoxide to react with 1-isobutyl-3-methylbenzene under pressure in the presence of triflic acid to directly introduce a formyl group at position 4.

CITATION LIST

Patent Literature

PTL1: JP 2017-533926A

SUMMARY OF INVENTION

Technical Problem

PTL 1 describes a method for producing 4-isobutyl-2-methylbenzaldehyde by reacting 1-isobutyl-3-methylbenzene with carbon monoxide under pressure in the presence of triflic acid. However, the Examples only describe reacting 1-isobutyl-3-methyl-4-benzene bromide with dimethylformamide to obtain 2-methyl-4-isobutylbenzaldehyde.

An object of the present invention is to provide a method for producing 2,4-dialkylbenzaldehyde with excellent conversion rate and yield, and excellent regioselectivity for formylation, by allowing carbon monoxide to react on a starting material containing a specific m-dialkylbenzene in the presence of hydrogen fluoride and boron trifluoride.

Solution to Problem

As a result of diligent investigation, the present inventors have found that a high conversion rate and yield can be obtained and an extremely regioselective formylation proceeds by allowing carbon monoxide to react on a starting material containing m-dialkylbenzene in the presence of hydrogen fluoride and boron trifluoride, with use of a specific m-dialkylbenzene as the starting material and through control of the amount of boron trifluoride added to m-dialkylbenzene within a specific range, and thus have completed the present invention.

In other words, the present invention is as follows.

<1> A method for producing 2,4-dialkylbenzaldehyde comprising a step of allowing carbon monoxide to react on a starting material containing m-dialkylbenzene represented by formula (1) in the presence of hydrogen fluoride and boron trifluoride for formylation at least at a position (a), wherein the starting material is a dialkylbenzene containing more than 90 mol % of m-dialkylbenzene represented by the formula (1), and the number of moles of boron trifluoride relative to 1 mole of m-dialkylbenzene represented by the formula (1) is 0.7 mol or more and 3.0 mol or less:

(1)

wherein $R^1$ represents an alkyl group having 1 or more and 3 or less carbon atoms, and $R^2$ represents a chain or cyclic alkyl group having 2 or more and 7 or less carbon atoms, with a secondary or tertiary carbon at the benzylic position, provided that the number of carbons of $R^2$ is larger than the number of carbons of $R^1$.

<2> The method for producing 2,4-dialkylbenzaldehyde according to claim 1, wherein the reaction temperature is −40° C. or higher and 10° C. or lower.

<3> The method for producing 2,4-dialkylbenzaldehyde according to <1> or <2>, wherein the number of moles of hydrogen fluoride relative to 1 mole of m-dialkylbenzene represented by the formula (1) is 2.5 mol or more and 20 mol or less.

<4> The method for producing 2,4-dialkylbenzaldehyde according to any of <1> to <3>, wherein $R^1$ is a methyl group or an ethyl group, and $R^2$ is an ethyl group, a n-propyl group, an isopropyl group, an isobutyl group, or a neopentyl group.

<5> The method for producing 2,4-dialkylbenzaldehyde according to any of <1> to <4>, wherein $R^1$ is a methyl group.

<6> The method for producing 2,4-dialkylbenzaldehyde according to any of <1> to <5>, wherein $R^1$ is a methyl group and $R^2$ is an isopropyl group, $R^1$ is a methyl group and $R^2$ is an isobutyl group, or $R^1$ is a methyl group and $R^2$ is a neopentyl group.

<7> The method for producing 2,4-dialkylbenzaldehyde according to any of <1> to <6>, wherein the content of 2,4-dialkylbenzaldehyde formylated at the position (a) in 2,4-dialkylbenzaldehyde obtained is 80 mol % or more.

Advantageous Effects of Invention

According to the present invention, a method for producing 2,4-dialkylbenzaldehyde with excellent conversion rate and yield, and excellent regioselectivity for formylation can be provided by allowing carbon monoxide to react on a starting material containing a specific m-dialkylbenzene in the presence of hydrogen fluoride and boron trifluoride.

DESCRIPTION OF EMBODIMENTS

Method for Producing 2,4-Dialkylbenzaldehyde

A method for producing 2,4-dialkylbenzaldehyde according to the present invention (hereinafter, also simply referred to as "the production method of the present invention") comprises a step of allowing carbon monoxide to react on a starting material containing m-dialkylbenzene represented by formula (1) in the presence of hydrogen fluoride and boron trifluoride for formylation at least at a position (a), wherein the starting material is a dialkylbenzene containing more than 90 mol % of m-dialkylbenzene represented by the formula (1), and the number of moles of boron trifluoride relative to 1 mole of m-dialkylbenzene represented by the formula (1) is 0.7 mol or more and 3.0 mol or less:

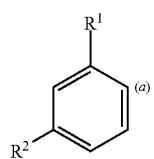

wherein $R^1$ represents an alkyl group having 1 or more and 3 or less carbon atoms, and $R^2$ represents a chain or cyclic alkyl group having 2 or more and 7 or less carbon atoms, with a secondary or tertiary carbon at the benzylic position, provided that the number of carbons of $R^2$ is larger than the number of carbons of $R^1$.

The reaction formula of the present invention is shown below:

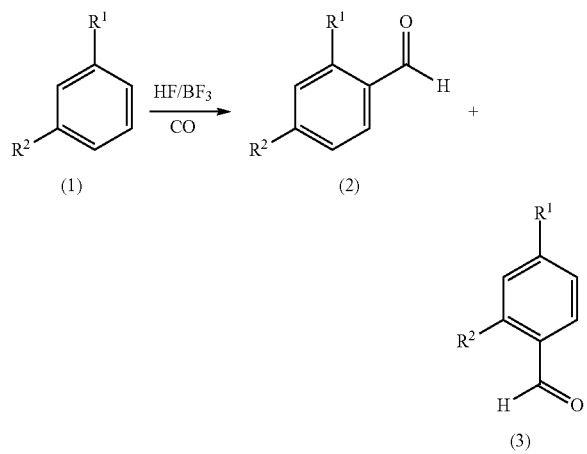

wherein $R^1$ represents an alkyl group having 1 or more and 3 or less carbon atoms, and $R^2$ represents a chain or cyclic alkyl group having 2 or more and 7 or less carbon atoms, with a secondary or tertiary carbon at a benzylic position, provided that the number of carbons of $R^2$ is larger than the number of carbons of $R^1$.

Generally, when m-dialkylbenzene is subjected to a formylation reaction, the compound is formylated at the para position (p-position) of each alkyl group to form a mixture of two isomers. Specifically, for example, when a compound such as the above formula (1) is formylated, a mixture of a compound represented by the formula (2) and a compound represented by the formula (3) is generally obtained as a reaction product. These compounds have similar physical properties, and due to difficulty in separation and purification, a production method is therefore desired in which formylation proceeds regioselectively to obtain the compound represented by the formula (2) in a high isomer ratio.

Further, in the formylation of the compound represented by the formula (1), a side reaction such as disproportionation reaction may occur.

According to the present invention, 2,4-dialkylbenzaldehyde (compound represented by the formula (2)) formylated at least at a position (a) can be obtained, and 2,4-dialkylbenzaldehyde (compound represented by the formula (2)) formylated at the position (a) at a high regioselectivity can be obtained.

Conventionally, as described in PTL 1, a method of functionalizing through bromination at the position (a), and a method of causing a reaction with carbon monoxide in the presence of triflic acid (trifluoromethanesulfonic acid) have been known. However, a lower-cost and high-efficiency production method with excellent conversion rate and yield, and excellent regioselectivity in formylation to achieve a high isomer ratio has been required.

The present inventors have found that 2,4-dialkylbenzaldehyde formylated at a position (a) with an extremely improved regioselectivity can be obtained at a high conversion rate and yield through formylation in which carbon monoxide is allowed to react with a starting material containing a specific amount or more of m-dialkylbenzene having a specific structure in the presence of hydrogen fluoride and boron trifluoride, while controlling the molar ratio of boron trifluoride relative to m-dialkylbenzene represented by the formula (1) within a specific range.

Although the detailed reason why the above reaction occurs is unknown, it is presumed that formylation at the position (a) is promoted because the substituent $R^2$ is more bulky than $R^1$ in the formula (1). However, it is extremely important that $R^1$ and $R^2$ are specific substituents. For example, it has been found that in the case of using tert-butyl as $R^2$, the yield decreases. A bulky substituent is not necessarily enough as $R^2$, and it is important that $R^2$ is a specific substituent having a secondary or tertiary carbon at a benzylic position.

It has been also found that the regioselectivity in formylation is improved by controlling the molar ratio of boron trifluoride relative to m-dialkylbenzene represented by the formula (1) within a specific range.

Hereinafter, the present invention will be described in detail.

Starting Material

In the present invention, the starting material contains m-dialkylbenzene represented by the following formula (1), and the starting material is a dialkylbenzene that contains more than 90 mol % of m-dialkylbenzene represented by the following formula (1) in the starting material.

The starting material may contain a dialkylbenzene having $R^1$ and $R^2$ as substituents such as p-dialkylbenzene having $R^1$ and $R^2$ at the para position (p-position) and o-dialkylbenzene having $R^1$ and $R^2$ at the ortho position (o-position) with a content of 10 mol % or less, in addition to m-dialkylbenzene represented by the formula (1).

The content of m-dialkylbenzene represented by the formula (1) in the starting material is more than 90 mol %, preferably 93 mol % or more, more preferably 96 mol % or more, and may be 100 mol %, from the viewpoint of obtaining 2,4-dialkylbenzaldehyde having few impurities and by-products, with excellent regioselectivity in formylation.

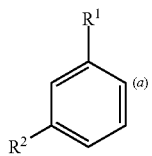

(1)

wherein $R^1$ represents an alkyl group having 1 or more and 3 or less carbon atoms, and $R^2$ represents a chain or cyclic alkyl group having 2 or more and 7 or less carbon atoms, with a secondary or tertiary carbon at a benzylic position, provided that the number of carbons of $R^2$ is larger than the number of carbons of $R^1$.

Compound Represented by Formula (1)

In the above formula (1), $R^1$ represents an alkyl group having 1 or more and 3 or less carbon atoms, and $R^2$ represents a chain or cyclic alkyl group having 2 or more and 7 or less carbon atoms with a secondary or tertiary carbon at a benzylic position, provided that the number of carbons of $R^2$ is larger than the number of carbons of $R^1$. In the present invention, the starting material contains more than 90 mol % of a compound represented by the formula (1) of which $R^1$ and $R^2$ are specific substituents, so that an extremely regioselective formylation reaction with excellent conversion rate and yield proceeds. Therefore, in the case of using a compound of which $R^2$ is a tert-butyl group, that is, a compound of which $R^2$ has a quaternary carbon atom at a benzyl position, the yield decreases.

From the viewpoint of reactivity, $R^1$ is preferably a methyl group or an ethyl group, more preferably a methyl group.

$R^2$ is a chain or cyclic alkyl group having 2 or more and 7 or less carbon atoms with a secondary or tertiary carbon at a benzyl position. The number of carbons is preferably 2 or more and 6 or less, more preferably 3 or more and 5 or less, from the viewpoint of reactivity and regioselectivity. Specific examples of $R^2$ include an ethyl group, a n-propyl group, an isopropyl group, a n-butyl group, a sec-butyl group, an isobutyl group, a n-pentyl group, a sec-pentyl group, a 3-pentyl group, an isopentyl group, a neopentyl group, a cyclopentyl group, and a cyclohexyl group. Among these, from the viewpoint of reactivity and regioselectivity, $R^2$ is preferably an ethyl group, a n-propyl group, an isopropyl group, an isobutyl group or a neopentyl group, more preferably a n-propyl group, an isopropyl group, an isobutyl group or a neopentyl group, still more preferably an isopropyl group, an isobutyl group or a neopentyl group, further preferably an isopropyl group or a neopentyl group, and furthermore preferably a neopentyl group.

In the compound represented by the formula (1), it is preferable that $R^1$ be a methyl group and $R^2$ be an isopropyl group, $R^1$ be a methyl group and $R^2$ be an isobutyl group, or $R^1$ be a methyl group and $R^2$ be a neopentyl group; it is more preferable that $R^1$ be a methyl group and $R^2$ be an isopropyl group, or $R^1$ be a methyl group and $R^2$ be a neopentyl group; and it is still more preferable that $R^1$ be a methyl group and $R^2$ be a neopentyl group.

Method for Producing Compound Represented by Formula (1)

Although a commercially available product may be used as the compound represented by the formula (1), a compound of which $R^1$ is a methyl group may be also synthesized, for example, as follows.

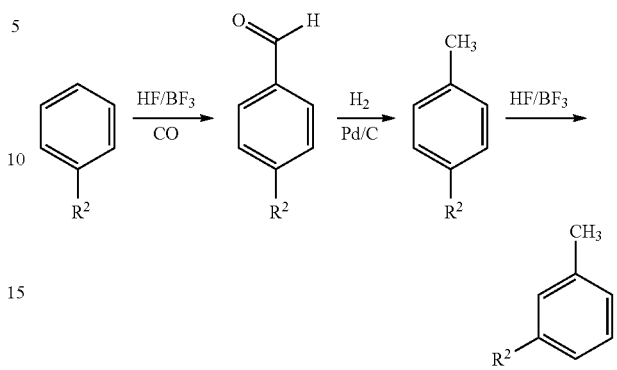

A benzene compound having $R^2$ as a substituent is reacted with carbon monoxide in the presence of hydrogen fluoride and boron trifluoride for formylation at the p-position of $R^2$ to obtain p-alkylbenzaldehyde.

Next, the resulting p-alkylbenzaldehyde is reduced in the presence of a palladium catalyst, so that the formyl group is reduced to a methyl group.

Further, the resulting p-dialkylbenzene is subjected to an isomerization reaction in the presence of hydrogen fluoride and boron trifluoride to isolate m-dialkylbenzene.

Boron Trifluoride

In the present invention, carbon monoxide is allowed to react on the starting material in the presence of hydrogen fluoride and boron trifluoride. On this occasion, the number of moles of boron trifluoride relative to 1 mole of m-dialkylbenzene represented by the formula (1) is 0.7 mol or more, preferably 0.8 mol or more, more preferably 1.2 mol or more, and still more preferably 1.4 mol or more, from the viewpoint of reactivity, and 3.0 mol or less, preferably 2.8 mol or less, more preferably 2.4 mol or less, and still more preferably 2.0 mol or less, from the viewpoint of improving the isomer ratio and economy.

Hydrogen Fluoride

Hydrogen fluoride (HF) has also a function as a solvent for the reaction. As the hydrogen fluoride, substantially anhydrous hydrogen fluoride is preferred from the viewpoint of reactivity. The term "substantially anhydrous" means that the content of water is 5 mass % or less, preferably 1 mass % or less, and more preferably 0.1 mass % or less.

The molar ratio of hydrogen fluoride relative to m-dialkylbenzene represented by the formula (1) as starting material (hydrogen fluoride/m-dialkylbenzene represented by formula (1)) is preferably 2.5 or more, more preferably 5.0 or more, and still more preferably 7.0 or more, from the viewpoints of reactivity with carbon monoxide and suppression of side reactions, and preferably 20.0 or less, more preferably 15.0 or less, and still more preferably 10.0 or less, from the viewpoints of economy and production efficiency.

Reaction Conditions

Reaction Temperature

In the present invention, carbon monoxide is allowed to react with a starting material containing m-dialkylbenzene represented by the formula (1) in the presence of hydrogen fluoride and boron trifluoride.

The temperature at which carbon monoxide acts during the reaction is preferably −40° C. or higher, more preferably −35° C. or higher, still more preferably −30° C. or higher, and preferably 10° C. or lower, more preferably 5° C. or lower, from the viewpoints of improving the reactivity, suppressing side reactions, and improving the regioselectivity for introduction of a formyl group.

In the case where the compound represented by the formula (1) is m-isobutyltoluene, the reaction temperature is preferably −40° C. or higher, more preferably −30° C. or higher, still more preferably −5° C. or higher, and preferably 10° C. or lower, more preferably 5° C. or lower, from the viewpoints of increasing a shielding effect and improving the regioselectivity for introduction of a formyl group.

Further, in the case where the compound represented by the formula (1) is m-neopentyltoluene, the difference in the shielding effect due to the temperature rise is small because the neopentyl group is bulky. Accordingly, the reaction temperature is preferably −30° C. or higher, more preferably −15° C. or higher, still more preferably −5° C. or higher, and preferably 10° C. or lower, more preferably 5° C. or lower.

Reaction Pressure

It is preferable that the reaction between the starting material and carbon monoxide be performed under pressure.

The pressure during the reaction as the partial pressure of carbon monoxide is preferably 1.0 MPaG or more, more preferably 1.5 MPaG or more, still more preferably 1.8 MPaG or more, and preferably 3.0 MPaG or less, more preferably 2.5 MPaG or less, still more preferably 2.2 MPaG or less, from the viewpoint of improving the reactivity and suppressing side reactions.

Reaction Time

In the present invention, the reaction time is not particularly limited, being preferably 10 minutes or more, more preferably 20 minutes or more, still more preferably 30 minutes or more, and preferably 24 hours or less, more preferably 12 hours or less, still more preferably 5 hours or less, from the viewpoints of sufficiently advancing the reaction, suppressing side reactions and decomposition of products, and efficiently producing the product.

Solvent

Also, the production method of the present invention may be performed in the presence of a solvent. The solvent for use is not particularly limited as long as it has good solubility for the starting material and is inactive to hydrogen fluoride and boron trifluoride. Examples thereof include a saturated aliphatic hydrocarbon such as hexane, heptane and decane, an aromatic hydrocarbon such as benzene and toluene, and a halogenated aliphatic hydrocarbon such as chloroform, methylene chloride and dichloroethane. These solvents may be used alone or in combination of two or more.

The amount of the solvent used is not particularly limited, and may be appropriately selected from the viewpoints of reaction uniformity, reaction rate, and solvent removal.

In the present invention, since hydrogen fluoride present during the reaction functions also as a solvent, no solvent may be used.

Reaction Mode

The mode of the production method of the present invention is not particularly limited, and any method such as a batch type, semi-batch type, continuous type, etc., may be employed. The continuous type is preferred due to the ability to recover and reuse a catalyst and from the viewpoint of production efficiency.

Further, the apparatus used in the production method is a reaction apparatus that can sufficiently mix a liquid phase and a gas phase while adjusting temperature under pressure.

For example, in the batch type, a starting material, hydrogen fluoride, boron trifluoride, and a solvent if necessary, are charged in a reactor with a stirrer, the contents are stirred, the liquid temperature is preferably maintained at −30° C. or higher and 10° C. or lower, then the pressure is preferably increased to 1.0 MPaG or more and 3.0 MPaG or less by carbon monoxide, subsequently the pressure and liquid temperature are maintained as they are and held for 10 minutes or more and 5 hours or less until carbon monoxide is no longer absorbed, and then the reaction product solution is discharged to obtain 2,4-dialkylbenzaldehyde.

Moreover, in the semi-batch type, hydrogen fluoride and boron trifluoride are charged in a reactor with a stirrer, the contents are stirred, the liquid temperature is preferably set to −30° C. or higher and 10° C. or lower, the temperature is allowed to be in a constant state, subsequently the pressure is preferably increased to 1.0 MPaG or more and 3.0 MPaG or less by carbon monoxide so that carbon monoxide can be supplied so as to keep the pressure constant. Then, a starting material dissolved in a solvent if necessary is supplied, and after the supply is completed, the reactant is held for 10 minutes or more and 5 hours or less until the absorption of carbon monoxide is completed followed by discharge of the reaction product liquid to obtain 2,4-dialkylbenzaldehyde.

Further, in the continuous type, first, hydrogen fluoride and boron trifluoride are charged into a reactor with a stirrer, the contents are stirred, the liquid temperature is preferably set to −30° C. or higher and 10° C. or lower, the temperature is allowed to be in a constant state, subsequently the pressure is preferably increased to 1.0 MPaG or more and 3.0 MPaG or less by carbon monoxide so that carbon monoxide can be supplied so as to keep the pressure constant. Then, a semi-batch reaction is carried out in which a starting material dissolved in a solvent if necessary is supplied. Further, hydrogen fluoride, boron trifluoride, and the starting material dissolved in the solvent, if necessary, are started to be supplied, and the reaction product liquid is continuously discharged. The time for the reaction liquid to stay in the reactor is preferably 10 minutes or more and 5 hours or less. By setting the residence time to 10 minutes or more and 5 hours or less, 2,4-dialkylbenzaldehyde can be efficiently produced.

After removing hydrogen fluoride and boron trifluoride from the obtained reaction liquid containing 2,4-dialkylbenzaldehyde, it can be purified by a conventional method such as distillation or extraction. Alternatively, in order to remove hydrogen fluoride from the reaction liquid, neutralizing washing with sodium hydroxide aqueous solution may be performed.

In the present invention, the conversion ratio indicates the degree of consumption of m-dialkylbenzene represented by the formula (1) contained in the starting material, being represented by the following formula.

Conversion ratio (mol %)={1-(Amount of substance of m-dialkylbenzene represented by formula (1) remaining after reaction (number of moles))/(Amount of substance of m-dialkylbenzene represented by formula (1) in starting material (number of moles))}×100

In the present invention, a high conversion ratio can be obtained by using a specific starting material and setting the number of moles of boron trifluoride relative to m-dialkylbenzene represented by the formula (1) within a specific range. The conversion ratio is preferably 70 mol % or more, more preferably 80 mol % or more, still more preferably 90 mol % or more, furthermore preferably 95 mol % or more, and 100 mol % or less.

In order to control the conversion rate within the above range, it is preferable to appropriately adjust the reaction temperature, reaction time, carbon monoxide pressure, amounts of hydrogen fluoride and boron trifluoride, etc.

2,4-Dialkylbenzaldehyde

In the production method of the present invention, formylation is performed at least at the position (a) in the formula (1). The following chemical formula is the formula (1) in which the substitution position is specified for illustrative purposes.

In general, when carbon monoxide is allowed to react on the starting material containing m-dialkylbenzene in the presence of hydrogen fluoride and boron trifluoride, formylation tends to occur at the position (c), which is the para position (p-position) of $R^1$, in addition to at the position (a) of the formula (1). On the other hand, formylation barely proceeds at the position (b), which is the meta position (m-position) of $R^1$ and $R^2$, and at the position (d), which is the ortho position (o-position) of $R^1$ and $R^2$.

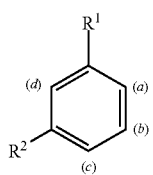

(1)

wherein $R^1$ represents an alkyl group having 1 or more and 3 or less carbon atoms, and $R^2$ represents a chain or cyclic alkyl group having 2 or more and 7 or less carbon atoms, with a secondary or tertiary carbon at the benzylic position, provided that the number of carbons of $R^2$ is larger than the number of carbons of $R^1$.

In the present invention, yield (mol %) represents the total amount of substance (number of moles) of the obtained dialkylbenzaldehyde relative to the amount of substance (number of moles) of m-dialkylbenzene represented by the formula (1) contained in the starting material, being indicated by the following expression.

Yield (mol %)={(Total amount of substance of the obtained dialkylbenzaldehyde (number of moles))/(Amount of substance of m-dialkylbenzene represented by the formula (1) in the starting material (number of moles))}×100

Here, the total amount of substance of the obtained dialkylbenzaldehyde means the total amount of substance of dialkylbenzaldehyde formylated at any of the above positions (a), (b), (c), and (d), which can be approximated as the total amount of substance of 2,4-dialkylbenzaldehyde formylated at the position (a) and 2,4-dialkylbenzaldehyde formylated at the position (c).

The yield decreases due to occurrence of a side reaction, for example, a disproportionation reaction (see JP 2005-120037 A).

In the present invention, a high yield can be obtained by using a specific starting material and setting the number of moles of boron trifluoride relative to m-dialkylbenzene represented by the formula (1) within a specific range. The yield is preferably 70 mol % or more, more preferably 80 mol % or more, still more preferably 90 mol % or more, furthermore preferably 95 mol % or more, and 100 mol % or less.

In order to keep the yield within the above range, it is preferable to appropriately adjust the reaction temperature, reaction time, carbon monoxide pressure, amounts of hydrogen fluoride and boron trifluoride, etc.

The isomer ratio (mol %) of 2,4-dialkylbenzaldehyde formylated at the position (a) means the amount of substance of 2,4-dialkylbenzaldehyde formylated at the position (a) (number of moles) relative to the total amount of substance of dialkylbenzaldehyde formylated at any of the positions (a), (b), (c), and (d) (number of moles). As described above, the total amount of substance (number of moles) of dialkylbenzaldehyde can be approximated as the total amount of substance (number of moles) of 2,4-dialkylbenzaldehyde formylated at the position (a) and 2,4-dialkylbenzaldehyde formylated at the position (c).

In the present invention, by using a specific starting material and setting the number of moles of boron trifluoride relative to m-dialkylbenzene represented by the formula (1) within a specific range, formylation occurs at the position (a) at a high regioselectivity, so that a high isomer ratio can be obtained. The isomer ratio (mol %) of the 2,4-dialkylbenzaldehyde formylated at the position (a) is preferably 60 mol % or more, more preferably 70 mol % or more, still more preferably 80 mol % or more, further preferably 85 mol % or more, furthermore preferably 90 mol % or more, furthermore preferably 95 mol % or more, and 100 mol % or less.

In order to control the isomer ratio within the above range, it is preferable to appropriately adjust the reaction temperature, reaction time, carbon monoxide pressure, amounts of hydrogen fluoride and boron trifluoride, etc.

The yield of 2,4-dialkylbenzaldehyde formylated at the position (a) is calculated from the yield and the isomer ratio as follows.

Yield (mol %) of 2,4-dialkylbenzaldehyde formylated at position (a)≅Yield (mol %)×Isomer ratio (mol %)/100

In the present invention, by using a specific starting material and setting the number of moles of boron trifluoride relative to m-dialkylbenzene represented by the formula (1) within a specific range, 2,4-dialkylbenzaldehyde formylated at the position (a) can be obtained at a high yield.

The yield (mol %) of 2,4-dialkylbenzaldehyde formylated at the position (a) is preferably 40 mol % or more, more preferably 50 mol % or more, still more preferably 60 mol % or more, further preferably 65 mol % or more, furthermore preferably 70 mol % or more, furthermore preferably 80 mol % or more, furthermore preferably 90 mol % or more, furthermore preferably 95 mol % or more, and 100 mol or less.

Improvement in the yield of 2,4-dialkylbenzaldehyde formylated at the position (a) is achieved by improving the yield and the isomer ratio, and it is preferable to appropriately adjust the reaction temperature, reaction time, carbon monoxide pressure, amounts of hydrogen fluoride, boron trifluoride, etc.

EXAMPLES

Hereinafter, the present invention will be described in more detail with reference to Examples, but the present invention is not limited to these Examples.

The reaction results were evaluated by the following expressions.

Conversion ratio (mol %)={1-(Amount of substance (number of moles) of starting material remaining after reaction)/(Amount of substance (number of moles) of starting material charged)}× 100

Yield (mol %)=(Amount of substance (number of moles) of 2,4-dialkylbenzaldehyde obtained)/ (Amount of substance (number of moles) of starting material charged)×100

In the calculation of the yield, "2,4-dialkylbenzaldehyde obtained" means total amount of substance (number of moles) of 2,4-dialkylbenzaldehyde formylated at the position (a) in the formula (1) and 2,4-dialkylbenzaldehyde formylated at the p-position of $R^1$ in the formula (1).

Isomer ratio (mol %) =(Amount of substance (number of moles) of 2,4-dialkylbenzaldehyde formylated at the position (a) in the formula (1))/(Total amount of substance (number of moles) of 2,4-dialkylbenzaldehyde obtained)× 100

It is noted that the amount of each substance (number of moles) was calculated by dividing the peak area by GC analysis by the molecular weight and taking the ratio thereof.

Further, the amount of substance (number of moles) of 2,4-dialkylbenzaldehyde formylated at the position (a) relative to the amount of substance (number of moles) of starting material charged was obtained by multiplying the yield by the isomer ratio.

Yield×Isomer ratio (mol %)=Yield (mol %)×Isomer ratio (mol %)/100

Gas Chromatography Analysis (GC Analysis)

Equipment: GC-2010 Plus (manufactured by Shimadzu Corporation)
Detector: FID
Column: DB-1 (Capillary Column manufactured by Agilent Technologies)
(0.32 mmφ×30 m×0.50 μm)
Temperature rising conditions: The temperature is raised at a rate of temperature rise of 5° C./min from 100° C. to 310° C. and the temperature is held at 310° C. for 20 minutes.

<NMR Spectrum Analysis>
Apparatus 1: Bruker Avance 2 600 MHz-NMR
(5 mm Cryo-CPDUL Probe) (manufactured by Bruker Corporation)
Apparatus 2: JEOL JNM-AL-400 400 MHz (manufactured by JEOL Ltd.)
Solvent: Deuterated chloroform ($CDCl_3$)
Measurement mode: $^1H$, $^{13}C$
Internal standard substance: Tetramethylsilane (TMS)

It is noted that apparatus 1 was used for the measurement of 4-isopropyl-2-methylbenzaldehyde, and apparatus 2 was used for the measurement of 4-isobutyl-2-methylbenzaldehyde and 4-neopentyl-2-methylbenzaldehyde.

Mass Spectrometry (GC-MS)

Equipment: GCMS-QP2010 Ultra (manufactured by Shimadzu Corporation)
Ionization method: EI Example 1

A 500 mL autoclave equipped with a NAC drive type stirrer, three inlet nozzles at the top and one outlet nozzle at the bottom, of which internal temperature can be controlled by a jacket, was used as the formylation reactor.

A refrigerant was passed through the jacket, and 120.5 g (6.02 mol) of hydrogen fluoride was charged into the autoclave cooled to −25° C.

Then, while stirring, 92.0 g (1.36 mol) of boron trifluoride was added while adjusting the temperature so as not to exceed −25° C.

After adding boron trifluoride, the temperature inside the autoclave was kept at −25° C. and the pressure was increased to 2.0 MPaG by carbon monoxide, and a mixed solution of 101.2 g (0.75 mol) of m-normal propyl toluene and 10.1 g of n-hexane was added thereto. As the m-normal propyl toluene, normal propyl toluene having a content of m-normal propyl toluene of 96.5 mass % was used, and 104.9 g of normal propyl toluene was added such that 101.2 g of m-normal propyl toluene was added.

After stirring for 50 minutes with a temperature of −25° C. and a pressure of 2.0 MPaG maintained, the reaction mixture in the autoclave was discharged into iced water. The discharged liquid was shaken well, and then an oil layer was separated. The obtained oil layer was washed with water for neutralization and then analyzed by gas chromatography (GC). As a result, the conversion ratio of m-normal propyl toluene was 97.4 mol %, and the total yield (yield) of two isomers including 4-normalpropyl-2-methylbenzaldehyde and 2-normalpropyl-4-methylbenzaldehyde was 95.6 mol %. Further, the amount of 4-normalpropyl-2-methylbenzaldehyde relative to the total amount of 4-normalpropyl-2-methylbenzaldehyde and 2-normalpropyl-4-methylbenzaldehyde (isomer ratio) was 72.5 mol %.

Examples 2 to 9, Comparative Examples 1 to 3

2,4-Dialkylbenzaldehyde was produced in the same manner as in Example 1 except that the reaction conditions, the types and amounts of various starting materials, catalysts, solvents, etc. used in the reaction used were changed as shown in Table 1.

The results are shown in Table 1.

The attribution of GC peaks was performed by GC-MS analysis (molecular weight) and NMR spectrum analysis.

The structure, NMR spectrum, and results of GC-MS analysis of 4-isopropyl-2-methylbenzaldehyde obtained as the main product in Example 2, 4-isobutyl-2-methylbenzaldehyde obtained as the main product in Examples 3 to 6, and 4-neopentyl-2-methylbenzaldehyde obtained as the main product in Examples 7 and 8, are shown below.

4-Isopropyl-2-Methylbenzaldehyde $^1$H NMR (600 MHz, CDCl$_3$) δ 1.26-1.27 (6H, d, J=6.6 Hz), 2.65 (3H, s), 2.89-2.96 (1H, sep, J=6.6 Hz), 7.11 (1H, s), 7.21-7.22 (1H, d, J=7.8 Hz), 7.72-7.73 (1H, d, J=7.8 Hz), 10.2 (1H, s)
$^{13}$C NMR (150 MHz, CDCl$_3$) δ 19.8, 23.6, 34.3, 124.4, 130.0, 132.3, 132.6, 140.8, 155.3, 192.4
MS(EI): m/z (%) 51(8), 65(13), 77(15), 91(49), 105(27), 119(65), 133(37), 147(100), 162(M$^+$, 95)

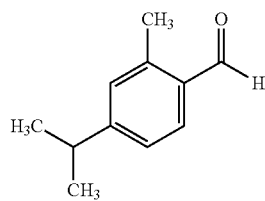

4-Isobutyl-2-Methylbenzaldehyde $^1$H NMR (400 MHz, CDCl$_3$) δ 0.91-0.92 (6H, d, J=6.8 Hz), 1.85-1.96 (1H, m), 2.49-2.51 (2H, d, J=7.2 Hz), 2.65 (3H, s), 7.03 (1H, s), 7.12-7.14 (1H, d, J=7.6 Hz), 7.70-7.72 (1H, d, J=7.6 Hz), 10.21 (1H, s)
$^{13}$C NMR (100 MHz, CDCl$_3$) δ 19.7, 22.4, 30.1, 45.4, 127.1, 132.2, 132.3, 132.6, 140.4, 148.3, 192.4
MS(EI): m/z (%) 43(23), 77(13), 91(37), 105(58), 134(100), 176(M$^+$, 77)

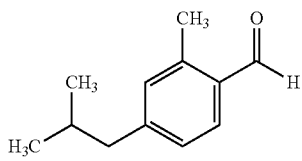

4-Neopentyl-2-Methylbenzaldehyde $^1$H NMR (400 MHz, CDCl$_3$) δ 0.92 (9H, s), 2.52 (2H, s), 2.65 (3H, s), 7.01 (1H, s), 7.11-7.13 (1H, d, J=7.6 Hz), 7.69-7.71 (1H, d, J=7.6 Hz), 10.23 (1H, s)
$^{13}$C NMR (100 MHz, CDCl$_3$) δ 19.7, 29.5, 32.1, 50.3, 128.5, 131.8, 132.3, 133.9, 139.9, 146.4, 192.5
MS(EI): m/z (%) 57(65), 77(8), 91(26), 105(40), 134(100), 175(11), 190(M$^+$, 29)

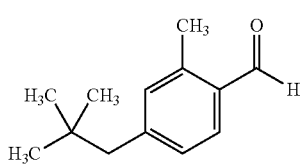

TABLE 1

| | | Example 1 | Example 2 | Example 3 | Example 4 | Example 5 | Example 6 | Example 7 |
|---|---|---|---|---|---|---|---|---|
| m-Dialkylbenzene | R$^1$ | Methyl | Methyl | Methyl | Methyl | Methyl | Methyl | Methyl |
| | R$^2$ | Normal propyl | Isopropyl | Isobutyl | Isobutyl | Isobutyl | Isobutyl | Neopentyl |
| Content of (1) in starting material [mol %] | | 96.5 | 100 | 99.0 | 99.0 | 99.0 | 99.0 | 97.0 |
| Amount charged | (1)(g) | 101.2 g | 86.4 g | 97.8 g | 100.8 g | 100.3 g | 50.2 g | 38.4 g |
| | [mol] | (0.75 mol) | (0.64 mol) | (0.66 mol) | (0.68 mol) | (0.68 mol) | (0.34 mol) | (0.24 mol) |
| | HF(g) | 120.5 g | 96.6 g | 104.6 g | 107.7 g | 107.7 g | 99.6 g | 35.5 g |
| | [mol] | (6.02 mol) | (4.83 mol) | (5.23 mol) | (5.38 mol) | (5.38 mol) | (4.98 mol) | (1.77 mol) |
| | BF$_3$(g) | 92.0 g | 65.5 g | 79.9 g | 82.3 g | 123.3 g | 21.3 g | 24.0 g |
| | [mol] | (1.36 mol) | (0.97 mol) | (1.18 mol) | (1.21 mol) | (1.82 mol) | (0.31 mol) | (0.35 mol) |
| | CO [MPaG] | 2.0 | 2.0 | 2.0 | 2.0 | 2.0 | 2.0 | 2.0 |
| | Solvent (g) | Hexane (10.1 g) | None | None | None | None | None | Heptane (38.4 g) |
| Reaction condition | HF/(1) [mol/mol] | 8.0 | 7.5 | 7.9 | 7.9 | 7.9 | 14.6 | 7.5 |
| | BF$_3$/(1) [mol/mol] | 1.8 | 1.5 | 1.8 | 1.8 | 2.7 | 0.9 | 1.5 |
| | Solvent/(1) [wt %] | 10.0 | None | None | None | None | None | 100.0 |
| | Reaction temperature [° C.] | −25.0 | −25.0 | −35.0 | 0.0 | 0.0 | 0.0 | 0.0 |
| | Reaction time [min] | 50.0 | 90.0 | 240.0 | 180.0 | 150.0 | 60.0 | 120.0 |
| | Pressure [MPaG] | 2.0 | 2.0 | 2.0 | 2.0 | 2.0 | 2.0 | 2.0 |
| Evaluation | Conversion ratio [mol %] | 97.4 | 98.9 | 93.8 | 99.8 | 100.0 | 72.4 | 98.5 |
| | Yield [mol %] | 95.6 | 90.4 | 93.5 | 99.2 | 99.6 | 72.1 | 97.9 |
| | Isomer ratio [mol %] | 72.5 | 89.1 | 76.8 | 83.9 | 82.7 | 86.4 | 98.6 |
| | Yield × Isomer ratio [mol %] | 69.3 | 80.5 | 71.8 | 83.2 | 82.4 | 62.3 | 96.5 |

TABLE 1-continued

|  |  | Example 8 | Example 9 | Comparative Example 1 | Comparative Example 2 | Comparative Example 3 |
|---|---|---|---|---|---|---|
| m-Dialkylbenzene | $R^1$ | Methyl | Methyl | Methyl | Methyl | Methyl |
|  | $R^2$ | Neopentyl | Ethyl | Isobutyl | Ethyl | Tertiary butyl |
| Content of (1) in starting material [mol %] | | 97.0 | 96.1 | 99.0 | 96.1 | 96.5 |
| Amount charged | (1)(g) | 47.1 g | 79.7 g | 50.0 g | 80.9 g | 85.6 g |
|  | [mol] | (0.29 mol) | (0.66 mol) | (0.34 mol) | (0.67 mol) | (0.58 mol) |
|  | HF(g) | 43.0 g | 99.4 g | 100.9 g | 100.9 g | 86.5 g |
|  | [mol] | (2.15 mol) | (4.97 mol) | (5.04 mol) | (5.04 mol) | (4.32 mol) |
|  | $BF_3$(g) | 29.5 g | 67.4 g | 13.8 g | 27.4 g | 27.4 g |
|  | [mol] | (0.44 mol) | (0.99 mol) | (0.20 mol) | (0.40 mol) | (0.58 mol) |
|  | CO [MPaG] | 2.0 | 2.0 | 2.0 | 2.0 | 2.0 |
|  | Solvent (g) | Heptane (47.1 g) | None | None | None | None |
| Reaction condition | HF/(1) [mol/mol] | 7.5 | 7.5 | 14.8 | 7.5 | 7.5 |
|  | $BF_3$/(1) [mol/mol] | 1.5 | 1.5 | 0.6 | 0.6 | 1.0 |
|  | Solvent/(1) [wt %] | 100.0 | None | None | None | None |
|  | Reaction temperature [° C.] | −25.0 | 0.0 | 0.0 | 0.0 | 0.0 |
|  | Reaction time [min] | 120.0 | 90.0 | 60.0 | 90.0 | 45.0 |
|  | Pressure [MPaG] | 2.0 | 2.0 | 2.0 | 2.0 | 2.0 |
| Evaluation | Conversion ratio [mol %] | 99.7 | 98.7 | 41.5 | 60.7 | 94.6 |
|  | Yield [mol %] | 98.6 | 98.1 | 41.2 | 48.6 | 4.7 |
|  | Isomer ratio [mol %] | 98.4 | 70.3 | 87.4 | 73.9 | 100 |
|  | Yield × Isomer ratio [mol %] | 97.0 | 69.0 | 36.0 | 35.9 | 4.7 |

As shown in the results in Table 1, according to the production method of the present invention, m-dialkylbenzene represented by the formula (1) was formylated into 2,4-dialkylbenzaldehyde at the position (a) in the formula (1) at a high conversion rate, a high yield, and a high isomer ratio.

On the other hand, in Comparative Examples 1 and 2 in which the molar ratio of boron trifluoride relative to m-dialkylbenzene represented by the formula (1) was less than 0.7, the conversion rates and yields were insufficient, so that the yield of 2,4-dialkylbenzaldehyde formylated at the position (a) in the formula (1) was low. Further, in Comparative Example 3 in which a starting material having a tert-butyl group as $R^2$ was used, the yield was low, so that the yield of 2,4-dialkylbenzaldehyde formylated at the position (a) in the formula (1) was low.

INDUSTRIAL APPLICABILITY

According to the present invention, a method for producing 2,4-dialkylbenzaldehyde with excellent conversion ratio, yield and regioselectivity by using a starting material containing m-dialkylbenzene can be provided. The 2,4-dialkylbenzaldehyde obtained is considered to be useful as a synthesis starting material compound such as a fragrance starting material.

The invention claimed is:

1. A method for producing 2,4-dialkylbenzaldehyde, comprising:
    allowing carbon monoxide to react on a starting material comprising m-dialkylbenzene represented by the following formula (1) in the presence of both hydrogen fluoride and boron trifluoride for formylation at least at a position (a),
    wherein the starting material is a dialkylbenzene comprising more than 90 mol % of m-dialkylbenzene represented by the formula (1), and
    wherein the number of moles of boron trifluoride relative to 1 mole of m-dialkylbenzene represented by the formula (1) is from 0.7 mol to 3.0 mol:

wherein $R^1$ represents an alkyl group having from 1 to 3 carbon atoms, and $R^2$ represents a chain or cyclic alkyl group having from 3 to 5 carbon atoms, with a secondary or tertiary carbon at a benzylic position, provided that the number of carbons of $R^2$ is greater than the number of carbons of $R^1$.

2. The method according to claim 1, wherein the reaction temperature is from −40° C. to 10° C.

3. The method according to claim 1, wherein the number of moles of hydrogen fluoride relative to 1 mole of m-dialkylbenzene represented by the formula (1) is from 2.5 mol to 20 mol.

4. The method according to claim 1, wherein $R^1$ is a methyl group or an ethyl group, and
    wherein $R^2$ is a n-propyl group, an isopropyl group, an isobutyl group, or a neopentyl group.

5. The method according to claim 1, wherein $R^1$ is a methyl group.

6. The method according to claim 1, wherein $R^1$ is a methyl group and $R^2$ is an isopropyl group, $R^1$ is a methyl group and $R^2$ is an isobutyl group, or $R^1$ is a methyl group and $R^2$ is a neopentyl group.

7. The method according to claim 1, wherein the content of 2,4-dialkylbenzaldehyde formylated at the position (a) in 2,4-dialkylbenzaldehyde obtained is at least 80 mol %.

8. The method according to claim 2, wherein the number of moles of hydrogen fluoride relative to 1 mole of m-dialkylbenzene represented by the formula (1) is from 2.5 mol to 20 mol.

9. The method according to claim 2, wherein $R^1$ is a methyl group or an ethyl group, and
wherein $R^2$ is a n-propyl group, an isopropyl group, an isobutyl group, or a neopentyl group.

10. The method according to claim 2, wherein $R^1$ is a methyl group.

11. The method according to claim 2, wherein $R^1$ is a methyl group and $R^2$ is an isopropyl group, $R^1$ is a methyl group and $R^2$ is an isobutyl group, or $R^1$ is a methyl group and $R^2$ is a neopentyl group.

12. The method according to claim 2, wherein the content of 2,4-dialkylbenzaldehyde formylated at the position (a) in 2,4-dialkylbenzaldehyde obtained is at least 80 mol %.

13. The method according to claim 3, wherein $R^1$ is a methyl group or an ethyl group, and
wherein $R^2$ is an ethyl group, a n-propyl group, an isopropyl group, an isobutyl group, or a neopentyl group.

14. The method according to claim 3, wherein $R^1$ is a methyl group.

15. The method according to claim 3, wherein $R^1$ is a methyl group and $R^2$ is an isopropyl group, $R^1$ is a methyl group and $R^2$ is an isobutyl group, or $R^1$ is a methyl group and $R^2$ is a neopentyl group.

16. The method according to claim 3, wherein the content of 2,4-dialkylbenzaldehyde formylated at the position (a) in 2,4-dialkylbenzaldehyde obtained is at least 80 mol %.

17. The method according to claim 4, wherein the content of 2,4-dialkylbenzaldehyde formylated at the position (a) in 2,4-dialkylbenzaldehyde obtained is at least 80 mol %.

18. The method according to claim 5, wherein the content of 2,4-dialkylbenzaldehyde formylated at the position (a) in 2,4-dialkylbenzaldehyde obtained is at least 80 mol %.

19. The method according to claim 6, wherein the content of 2,4-dialkylbenzaldehyde formylated at the position (a) in 2,4-dialkylbenzaldehyde obtained is at least 80 mol %.

20. The method according to claim 8, wherein $R^1$ is a methyl group and $R^2$ is an isopropyl group, $R^1$ is a methyl group and $R^2$ is an isobutyl group, or $R^1$ is a methyl group and $R^2$ is a neopentyl group.

21. The method according to claim 1, wherein $R^1$ is a methyl group and $R^2$ is an isopropyl group, or $R^1$ is a methyl group and $R^2$ is a neopentyl group.

* * * * *